(12) United States Patent
Zong et al.

(10) Patent No.: US 9,585,582 B2
(45) Date of Patent: Mar. 7, 2017

(54) METHOD AND SYSTEM TO FULLY-AUTOMATICALLY MEASURE THE ST-SEGMENT LEVEL OF ELECTROCARDIOGRAMS IN REAL-TIME ECG MONITORING

(71) Applicant: KONINKLIJKE PHILIPS N.V., Eindhoven (NL)

(72) Inventors: Wei Zong, Belmont, MA (US); Jyh-Yun John Wang, Newton, MA (US); Stephen Scott Kresge, West Newbury, MA (US); Haisheng Lu, Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 104 days.

(21) Appl. No.: 14/349,665

(22) PCT Filed: Oct. 5, 2012

(86) PCT No.: PCT/IB2012/055376
§ 371 (c)(1),
(2) Date: Apr. 4, 2014

(87) PCT Pub. No.: WO2013/054242
PCT Pub. Date: Apr. 18, 2013

(65) Prior Publication Data
US 2014/0249437 A1 Sep. 4, 2014

Related U.S. Application Data

(60) Provisional application No. 61/546,280, filed on Oct. 12, 2011.

(51) Int. Cl.
*A61B 5/00* (2006.01)
*A61B 5/04* (2006.01)
(Continued)

(52) U.S. Cl.
CPC ...... *A61B 5/04015* (2013.01); *A61B 5/04012* (2013.01); *A61B 5/0452* (2013.01);
(Continued)

(58) Field of Classification Search
USPC .................................................. 600/509, 516
See application file for complete search history.

(56) References Cited

U.S. PATENT DOCUMENTS 5,827,196 A 10/1998 Yeo et al.
6,263,235 B1 7/2001 Kaiser et al.
(Continued)

FOREIGN PATENT DOCUMENTS

JP 8182660 7/1996

OTHER PUBLICATIONS

Gordhandas, A. J., et al.; Rel-Time Extraction and Analysis of Key Morphological Features in the Electrocardiogram, for Data Compression and Clinical Decision Support; 2011; Spring Symposium: Computational Physiology; pp. 15-18.
(Continued)

*Primary Examiner* — Nicole F Johnson (57) ABSTRACT

A system for determining the Q and J points of an electrocardiogram (ECG) combines a WLT-based Q, J detection algorithm with signal quality assessment for lead selection. A Q, J detector (24) receives a beat-cycle waveform for the beat under consideration from each of a plurality (N) of ECG leads, and assesses signal quality for each lead using signal quality assessor (SQA) components $26_1$, $26_2$ ... $26_N$. The leads with "good" signal qualities are employed for a multichannel waveform length transform (WLT), which yields a combined waveform length signal (CWLS). The Q and J points are then determined from the CWLS.

19 Claims, 9 Drawing Sheets

(51) Int. Cl.
*A61B 5/0452* (2006.01)
*A61B 5/0472* (2006.01)
*A61B 5/0456* (2006.01)

(52) U.S. Cl.
CPC .......... *A61B 5/0456* (2013.01); *A61B 5/0472* (2013.01); *A61B 5/7221* (2013.01); *A61B 5/7253* (2013.01); *A61B 5/7278* (2013.01); *A61B 5/7203* (2013.01)

(56) References Cited

U.S. PATENT DOCUMENTS

| | | | |
|---|---|---|---|
| 6,901,285 | B2 | 5/2005 | Schreck |
| 7,539,535 | B1 | 5/2009 | Schlegel et al. |
| 8,805,482 | B2 | 8/2014 | Sitzman |
| 2006/0276716 | A1 | 12/2006 | Healey et al. |
| 2007/0239220 | A1* | 10/2007 | Greenhut ............. A61B 5/0452 607/32 |
| 2008/0194978 | A1 | 8/2008 | Beker et al. |
| 2009/0018459 | A1* | 1/2009 | Tseng ................... A61B 5/0468 600/516 |

OTHER PUBLICATIONS

Jager, F., et al.; Detection of Transient ST Segment Episodes During Ambulatory ECG Monitoring; 1998; Computers and Biomedical Research; 31:305-322.

Li, H., et al.; Body Sensor Network Based Context Aware QRS Detection; 2006; Proc. of 28th IEEE EMBS Conf.; pp. 3266-3269.

Smrdel, A., et al.; Advanced Detection of ST Segment Episodes in 24-Hour Ambulatory ECG Data by Automated Tracking of Transient ST Segment Reference Level; 2002; Computers in Cardiology; 29:325-328.

Zong, W., et al.; A QT Interval Detection Algorithm Based on ECG Curve Length Transform; 2006; Computers in Cardiology; 33:377-380.

Zong, W., et al.; A Robust Open-source Algorithm to Detect Onset and Duration of QRS Complexes; 2003; Computers in Cardiology; 30:737-740.

* cited by examiner

METHOD AND SYSTEM TO FULLY-AUTOMATICALLY MEASURE THE ST-SEGMENT LEVEL OF ELECTROCARDIOGRAMS IN REAL-TIME ECG MONITORING

CROSS REFERENCE TO RELATED APPLICATIONS

This application is a national filing of PCT application Ser. No. PCT/IB2012/055376, filed Oct. 5, 2012, published as WO 2013/054242 A1 on Apr. 18, 2013, which claims the benefit of U.S. provisional application Ser. No. 61/546,280 filed Oct. 12, 2011, which is incorporated herein by reference.

The present application relates generally to electrocardiography. It finds particular application in conjunction with the measurement of the ST-segment level of electrocardiograms (ECGs) in real-time and will be described with particular reference thereto. However, it is to be understood that it also finds application in other usage scenarios and is not necessarily limited to the aforementioned application.

An ECG is a recording of the electrical activity of the heart over a period of time. An electrocardiograph or other suitable electrical transducer non-invasively measures such electrical activity, and the recording is generated therefrom and/or by another device, such as a computer. Conventional electrocardiographs employ ten electrodes for measuring the electrical activity of the heart. Each electrode is placed on a patient at a particular location within some tolerance. From these ten electrodes, twelve leads (i.e., potential differences) are measured and/or derived. Other conventional electrocardiographs include three, five, fifteen, sixteen, EASI, etc. leads.

Figure 1:
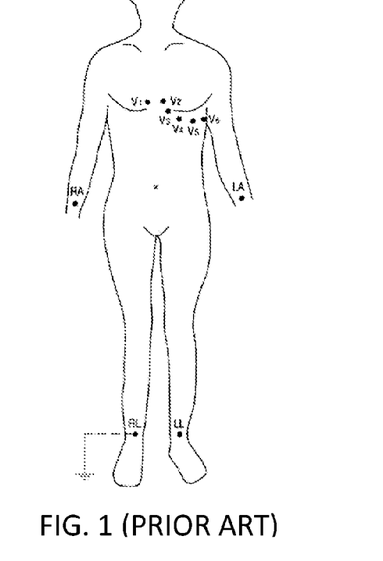
FIG. 1 is a graphical representation of the placement of electrodes on a patient for a conventional twelve lead electrocardiograph.

With reference to FIG. 1, the exemplary placement of electrodes on a patient for a conventional twelve lead electrocardiograph is illustrated. A right leg electrode RL serves as a ground for the other electrodes. Lead I is measured from a right arm electrode RA to a left arm electrode LA; lead II is measured from the right arm electrode RA to a left leg electrode LL; and lead III is measured from the left arm electrode LA to the left leg electrode LL. The average voltage V of the right arm electrode RA, the left arm electrode LA and the left leg electrode LL (i.e., Wilson's central terminal) is determined. The other nine leads include six precordial leads derived from potential differences between V and electrodes $V_{1-6}$ and three augmented limb leads aVR, aVL and aVF derived from combinations of leads I, II, and III. For real-time ECG monitoring, the 4 limb electrodes (RA, LA, RL, LL) are normally placed on the trunk near the corresponding limbs (known as the Mason-Liker lead placement) to reduce motion artifacts.

The ST-segment level of electrocardiograms is typically employed to screen and diagnose cardiovascular disease, such as myocardial infarction, cardiac ischemia, and so on. It is an important feature of electrocardiograms that is widely used in diagnostic ECG examination, ambulatory ECG examination, and real-time ECG monitoring. The ST-segment level of a selected, normal beat for an ECG lead is the voltage difference between the J+x point and the Iso-electric point. The J point is the offset or end point of the QRS complex and x is a selected time interval which varies from 0 to 80 ms; typically, x is chosen as 60 or 80 ms. The Iso-electric point is a time point before the QRS onset Q or start point of the QRS complex and after the end of the P wave. In practical clinical application, the Iso-electric point is usually equal to Q−20 ms for adult subjects.

One challenge with reliably measuring the ST-segment level is reliably locating the Iso-electric point and the J point. There are at least two approaches to determine these points in the real-time and ambulatory ECG monitoring, a manual approach and an automatic approach.

In the manual approach, the Iso-electric point is determined by subtracting a fixed time interval u (e.g., u=40 ms) from the QRS peak time R (i.e., Iso=R−u). The J point is determined by adding a fixed time interval z (e.g., z=80 ms) to the QRS peak time R (i.e., J=R+z). The fixed time intervals u and z are manually determined for each patient, usually at the beginning of the monitoring. However, this approach is less than desirable. It introduces extra work load to clinicians. Further, once the u and z offsets have been set, they stay fixed and do not adapt to changes of QRS morphology. Change in QRS morphology may prevent ST measurement at J and/or cause substantial error to occur for ST measurements at J. This, in turn, could cause false ST alarms and/or true ST events to be missed.

In the automatic approach, the Iso-electric point and the J point are automatically detected from an averaged beat-cycle ECG waveform of selected non-noisy normal beats in a predefined time window. This includes selection of non-noisy normal beats, sequential construction of a normal averaged beat, automatic searching for the Iso-electric point and the J point, and calculation of the ST-segment level for each ECG lead.

The selection of non-noisy normal beats involves noise detection for the ECG signals. One approach employs an algorithm that, for each lead, derives a 5-dimensional Karhunen-Loeve transform (KLT) feature vector for the ST segment s(i) and another 5-dimensional feature vector for the QRS complex q(i). For a given beat, s(i) and q(i) are compared to those of the neighboring beats, and the normalized residual error for the ST segment $r_s(i)$ and for the QRS complex $r_q(i)$ are calculated. The algorithm considers beat i noisy if the residual error, $r_s(i)$ or $r_q(i)$, exceeds a certain percentage (e.g. 25%). This method needs to use information of neighboring beats and assumes that most neighboring beats are non-noisy beats. The amount of calculation for deriving s(i) and q(i) is relatively high.

Another approach for ECG noise detection assesses the signal quality by major wave sharpness, high-frequency noise level, and low-frequency noise level of each ECG lead in the beat cycle. The major wave sharpness is measured by the maximum absolute amplitude divided by the absolute waveform area in a predefined window block (e.g., 400 ms). The high-frequency noise (HFN) level is calculated by summarizing a high-pass (2nd difference) filter of ECG signal absolute value in a one second time window centered with the R wave and dividing the sum with the absolute R wave amplitude. The low-frequency noise (LFN) level is measured by summarizing a low-pass filtered ECG signal absolute value in the one second time window and dividing the sum with the absolute R wave amplitude.

A challenge with this method is that, as the HFN and LFN are scaled by the absolute R wave amplitude to normalize them, the same amount of HFN and LFN will appear quite different under different absolute R wave amplitudes. When the R wave amplitude is very low, non-severe HFN and LFN values will appear severe. When the R wave amplitude is very large, severe HFN and LFN values will appear non-severe. As should be appreciated, both of these scenarios are undesirable and will generate incorrect noise estimation.

The construction of sequential averaged beats creates an averaged normal beat waveform in a predefined window. This is for further reducing ECG noise level to facilitate automatic searching for the Iso-electric points and the J points. Typically, a time window of 15 seconds is used. For each window, an averaged normal beat waveform is constructed by averaging all the selected normal beats.

The automatic searching for the Iso-electric points and the J points can be performed using numerous approaches. One approach determines the Iso-electric point by searching backward from a computer-detected QRS position R to R−108 ms for the "flattest" five-sample segment of each ECG lead. The middle sample of this segment is taken as the Iso-electric point candidate for the lead. Additional rules can be employed to determine a final Iso-electric point for all leads. Further, the J-point is determined by searching forward in each ECG lead from R to R+100 ms for the sample that the waveform starts to "flatten" based on the amount of consecutive signal voltage change. This sample is considered the J point for the ECG lead. The positions of the J points of all leads are compared and the position being the latest (i.e., furthest from R) is taken as the final J point for all leads.

One challenge with this approach is that it determines the Iso-electric point and the J point by tracking their direct features on the waveform of each ECG lead. However, this is time-consuming (i.e., the computational load is high) because it needs to go through each lead. Another challenge is that the final J point position may be easily corrupted when one lead has unusual QRS morphology or by local noise that causes a late "flatten" point. Yet another challenge is that this approach requires beat averaging to smooth the waveforms, so beat-to-beat ST measurements are not available.

As the Iso-electric point can be easily defined from the QRS onset (Q), an approach searching for the Iso-electric point and the J point can turn to detection of Q and J points. An effective and efficient QRS onset and offset (Q, J) detection employs a waveform length transform (WLT) that can convert multi-lead ECG signals into a single channel combined waveform length signal (CWLS). The CWLS preserves the QRS onset and offset features in a "global" way by taking into account the QRS morphologies of all ECG leads. The Q and J points are then detected from the CWLS. One challenge is that with multiple ECG leads, one noisy or poor quality lead can substantially corrupt the accuracy of the Q, J detection. Therefore, without an additional signal quality control process, this approach would not be suitable for reliable detection of the Iso-electric point and the J point.

The last component, calculation of the ST-segment level of each lead, is routine, given the Iso-electric point and the J point are appropriately obtained. As noted above, the ST-segment level of a selected, normal beat for an ECG lead is the voltage difference between the J+x point and the Iso-electric point of the ECG waveform of the lead, where x is a selected time interval, typically 60 or 80 ms.

The present application provides a new and improved method which overcomes the above-referenced problems and others.

In accordance with one aspect, a system determines the Q and J points of an electrocardiogram (ECG). The system includes at least one processor. The processor is programmed to receive beat-cycle waveforms for a selected beat from a plurality of ECG leads. Signal quality is determined for each of the plurality of ECG leads and the beat-cycle waveforms of ECG leads with signal quality meeting or exceeding predetermined signal quality criteria are combined. The Q and J points are identified on the combined beat-cycle waveform.

In accordance with another aspect, a method determines the Q and J points of an electrocardiogram (ECG). The method includes receiving beat-cycle waveforms for a selected beat from a plurality of ECG leads. Signal quality is determined for each of the plurality of ECG leads and the beat-cycle waveforms of ECG leads with signal quality meeting or exceeding a predetermined signal quality criteria are combined. The Q and J points are identified on the combined beat-cycle waveform.

One advantage resides in robust lead selection for ST-segment level measurements.

Another advantage resides in improved noise detection for lead selection.

Another advantage resides in noise tolerance for ST-segment level measurements.

Another advantage resides in independence from neighboring beats for lead selection.

Another advantage resides in improved accuracy in ST-segment level measurements for averaged beats and single beats.

Another advantage resides in detection of QRS width.

Another advantage resides in beat-to-beat ST-segment level measurements.

Another advantage resides in Q, J detection using all ECG leads with good signal quality.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 2:
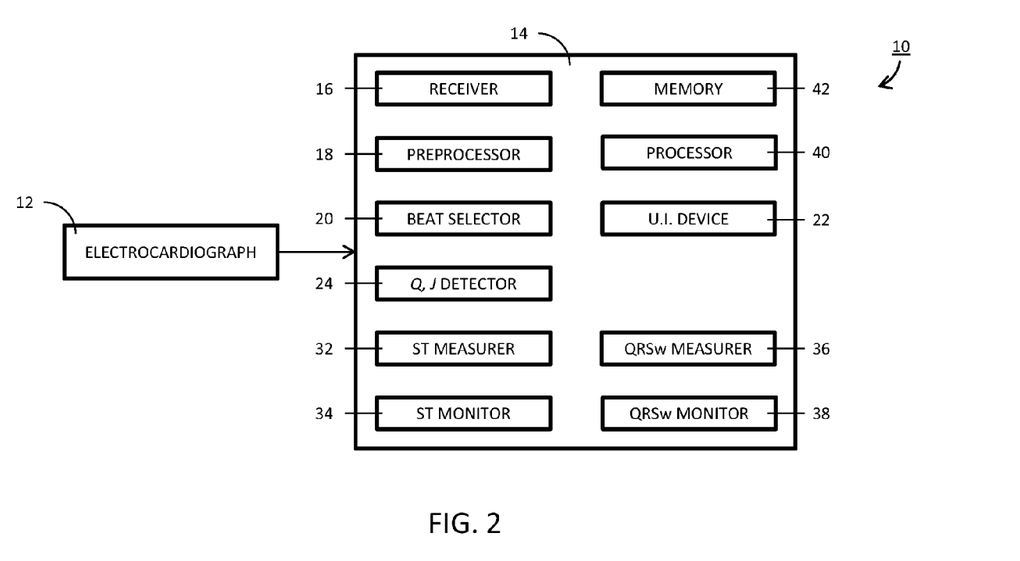
FIG. 2 is a block diagram of a multi-lead electrocardiography system.

With reference to FIG. 2, a multi-lead electrocardiography system 10 includes one or more sources 12 of electrocardiograms. Examples of suitable sources include an electrocardiograph, a Holter monitor, a defibrillator, a computer, a memory, an ECG monitor, a software component, and so on. The sources 12 may generate the electrocardiograms in real time and/or act as stores for the electrocardiograms.

An electrocardiogram analysis system (EAS) 14 receives the electrocardiograms from the sources 12 and measures the ST-segment level and/or QRS width of the electrocardiograms. It combines a WLT-based Q, J detection algorithm with signal quality assessment for lead selection. Only those leads with good signal quality are taken into account for Q, J detection. As discussed below, this yields reliable and efficient Q, J detection results. The EAS 14 can be used for real time or offline measurement of the ST-segment level and/or QRS width.

A receiver 16 of the EAS 14 receives each of the electrocardiograms from the sources 12. An electrocardiogram includes N ECG waveforms corresponding to N leads. N is greater than 1 and usually ranges from 3 to 8. The waveforms can be analog and/or digital depending upon the source. As to the former, the receiver 16 includes analog to digital converters that sample the analog waveforms at a predetermine rate. As to the latter, the waveforms are sampled at a predetermined rate.

Upon receiving an electrocardiogram, a preprocessor 18 detects and classifies each beat. Types of beats include, for example, a normal beat, an abnormal beat (such as premature ventricular contraction or PVC), and so on. In some embodiments, detection and classification is determined through analysis of the waveforms for a subset of the leads. For example, only the waveforms for one or two of the leads are used. Further, in some embodiments, the preprocessor 18 filters the waveforms to remove and/or reduce unwanted noises before detection and classification.

A beat selector 20 selects the beat-cycle waveforms from the preprocessed waveforms for a beat under consideration. The beat under consideration can be manually specified, for example, using a user input device 22, or automatically specified according to one or more rules. For example, every predetermined number of beats is considered where the predetermined number is greater than zero.

For the purpose of ST measurement, the considered beat is an individual normal beat or an averaged normal beat. For the purpose of QRS width measurement, the considered beat is an individual normal beat, an averaged normal beat, or an individual beat of any other type. An averaged normal beat can be determined by averaging the waveforms of the normal beats in a window of a predetermined size. For example, the beat-cycle waveform of an averaged normal beat can be obtained by averaging the normal beats in a prior 15-second window. The window can also be measured in heart beats, such as a 15 heart beat window.

In some embodiments, the beat-cycle waveforms for a considered beat are selected based on its QRS position in terms of the QRS-peak R. The beat-cycle waveforms are taken in the region of [R−f, R+g], where f and g are time intervals. The time intervals can be fixed or dynamically determined. For example, f and g can be 500 ms and 800 ms, respectively, for adult patients. As another example, f and g can be determined based on, for example, patient heart rate, e.g., shorter than the example for faster than normal heart rates and longer for slower than normal heart rates.

A Q, J detector 24 assesses signal quality of each lead based on the received beat-cycle waveforms. The leads with "good" signal qualities are employed for a multichannel waveform length transform (WLT), which yields a combined waveform length signal (CWLS). The Q and J points are then determined from the CWLS.

Figure 3:
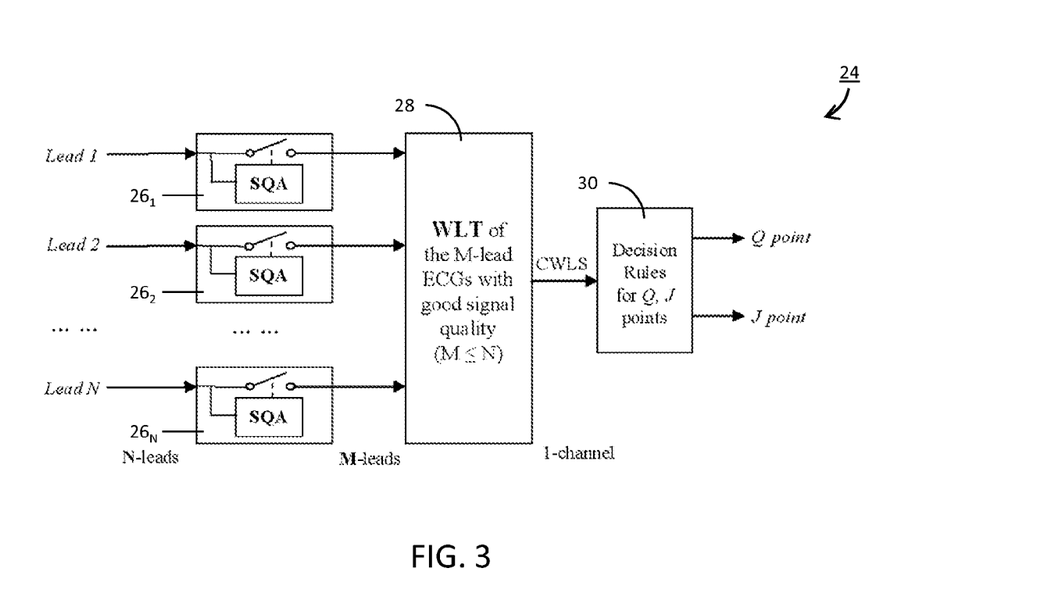
FIG. 3 is a block diagram of a Q, J detector.

With reference to FIG. 3, the Q, J detector 24 is illustrated. The Q, J detector 26 receives a beat-cycle waveform for the beat under consideration from each of the N leads. One or more signal quality assessor (SQA) components $26_1$, $26_2$, ..., $26_N$ then assess the signal quality of each lead. As illustrated, each lead includes a SQA component (SQA). However, it is to be understood that multi-lead SQA components are also contemplated. For example, a single SQA component can be employed for all the leads. Signal quality for a lead is typically assessed in terms of one or more of the following features: a) high-frequency noise level; b) low-frequency noise level; and c) QRS amplitude.

The high-frequency noise (HFN) level of a lead is measured by summing the second order difference of the corresponding beat-cycle waveform with exclusion of the QRS duration. One implementation is given by Equation (1).

$$HFN = \sum_{i=w1}^{w2} |dx^2[i]| + \sum_{i=w3}^{w4} |dx^2[i]|, \quad (1)$$

where $dx^2[i]=ecg[i]-(2\times ecg[i-1])+ecg[i-2]$, i is a time index in samples, ecg[i] is the $i^{th}$ sample of the beat-cycle waveform, w1, w2, w3, and w4 are time window boundaries in unit of samples as defined by: w1=R+2−(304 ms/si), w2=R−(96 ms/si), w3=R+(96 ms/si), w4=R+(304 ms/si), R is the QRS peak time (in sample) of the beat cycle waveform, and si is the sampling interval in ms. Notably, w1 and w2 define a first interval relative to R and w3 and w4 define a second interval relative to R.

The low-frequency noise (LFN) level of a lead is measured by summing a recursively smoothed beat-cycle waveform. Equation (2) gives one implementation.

$$LFN = \sum_{i=w1}^{w2} |y[i]|, \quad (2)$$

where y[i]=y[i−1]+(ecg[i]−y[i−1])/L, i is a time index, ecg[i] is the $i^{th}$ sample of the beat-cycle waveform, w1 and w2 are time window boundaries in unit of samples as defined by: w1=R−(304 ms/si), w2=R+(304 ms/si), R is the QRS peak time (in sample) of the beat cycle waveform, L=128 ms/si, y[w1−1] is a previously smoothed value, and si is the sampling interval in ms. Again, w1 and w2 define an interval relative to R.

The QRS amplitude (QRS_amp) of a lead is determined by taking the maximum difference between values of the beat-cycle waveform within a QRS region. In other words, the minimum value and the maximum value of the beat-cycle waveform within the QRS region are determined. The QRS amplitude is then the difference between these extremes. In some embodiments, the QRS region is [R−96 ms, R+96 ms], which covers the whole QRS duration for a normal beat.

The above HFN, LFN, and QRS_amp of a lead are scaled to physical units according to the sampling interval and resolution on the leads. In some embodiments, a high-frequency noise threshold (hfn_thr), a low-frequency noise threshold (lfn_thr), and a QRS amplitude threshold (qrs_amp_thr) are established, for example, based on experiments (e.g., qrs_amp_thr is chosen 0.4 mV). The scaled HFN, LFN, and QRS_amp are then compared to hfn_thr, lfn_thr, and qrs_amp_thr, respectively. A lead is labeled as "good" only if the HFN is less than hnf_thr, LFN is less than lfn_thr, and QRS_amp is larger than qrs_amp_thr. Otherwise, the lead is labeled as "poor". It is also contemplated that leads can also be labeled "good" based on other criteria for low high frequency noise, low low frequency noise and high QRS complex amplitude.

When a lead is determined to have good signal quality, the corresponding SQA component passes the lead to a waveform length transform (WLT) component. In that regard, the SQA components $26_1, 26_2, \ldots, 26_N$ can be viewed as gates for the leads. A WLT component 28 transforms the waveforms for M leads received from the SQA components $26_1, 26_2, \ldots, 26_N$ to a single channel combined waveform length signal (CWLS). Notably, M is less than or equal to N. QRS onset and offset detection is then done via the CWLS to produce the QRS onset (Q-point) and QRS offset (J-point) for the considered beat.

For a considered beat marked by its QRS peak R, the CWLS[i] is, as an embodiment for adult subjects, calculated in the region [R−200 ms, R+200 ms] according to Equation (3).

$$CWLS[i] = \sum_{k=i-w}^{i} \sqrt{\sum_{j=1}^{M} (\Delta t^2 + \Delta y_{j,k}^2)}, \quad (3)$$

Where i is a time index, w is a window in unit of samples as defined as: w=(144 ms/Δt), $\Delta y_{j,k}=ecg_j[k]−ecg_j[k−1]$, $ecg_j[k]$ is the lead j waveform at sample k, M is the number of leads, and Δt is the sampling interval in ms. Notably, the M leads used in Equation (3) are those leads labeled "good". Therefore, noisy and/or low amplitude leads are excluded to ensure uncorrupted CWLS.

Figure 4:
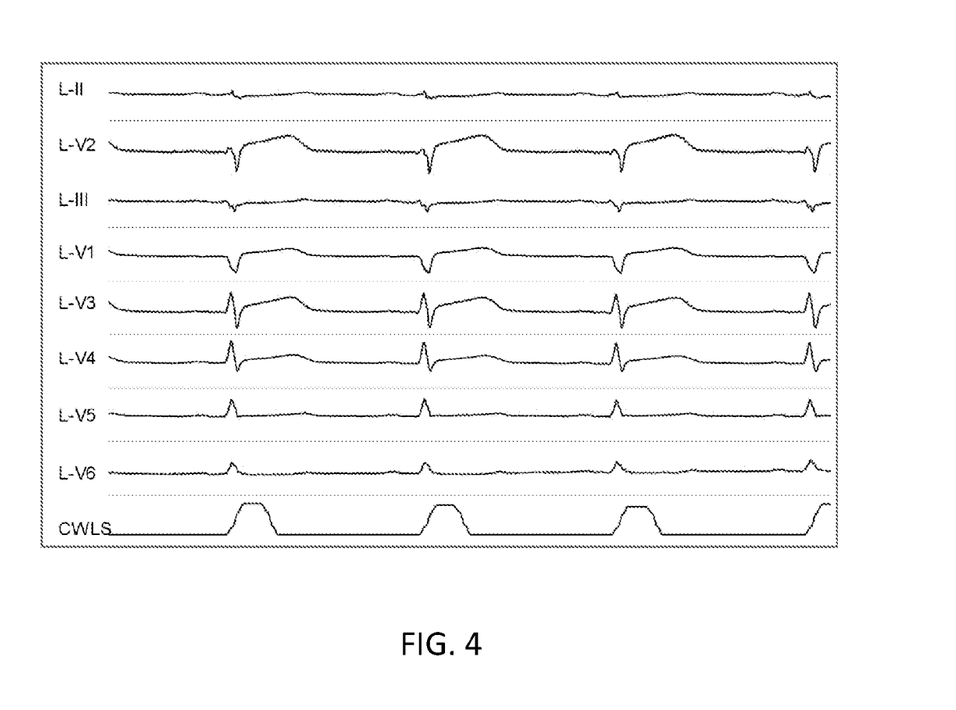
FIG. 4 is a graph of a combined waveform length signal versus eight ECG signals.

With reference to FIG. 4, an example of a CWLS versus eight ECG signals corresponding to eight different leads is provided. Traces 1 through 8 from top down are the input ECG signals in terms of Lead II, $V_2$, III, $V_1$, $V_3$, $V_4$, $V_5$, and $V_6$, respectively. The bottom trace is the CWLS that comes from 7 of the 8 leads. Lead II is excluded because it has poor signal quality from its low QRS amplitude (i.e., 0.25 mV<qrs_amp_thr).

The up-going portion of a CWLS theoretically and mathematically corresponds to the QRS duration. Therefore, the locations of onset and offset of the up-going portion of a CWLS correspond to the onset (Q) and offset (J) of QRS, respectively. A detection component 30 includes one or more rules implementing the approaches described hereafter for detection of the onset and the offset.

One approach for locating the onset of the up-going portion of a CWLS includes finding the maximal value (Lt_max) of the CWLS in the region of [R−200 ms, R+200 ms]. A virtual line is then drawn that connects two points on the CWLS. One point is at R−200 ms and the other is at a Mid-Lt-Point. The Mid-Lt-Point is the point where the CWLS value is firstly equal to or larger than Lt_max/2. The Mid-Lt-Point can be determined with a forward search from R−200 ms. The time point with the maximum distance between the CWLS and the virtual line in the region of [R−200 ms, Mid-Lt-Point] is then determined. This time point corresponds to the Q point. In some embodiments, an offset is applied to the time point to achieve the final Q point.

One approach for locating the offset of the up-going portion of a CWLS includes searching in a backward fashion on the CWLS from Lt_max to Mid-Lt-Point for the time point at which CWLS is firstly equal to or less than 99% of Ls_max. This time point corresponds to the J point. In some embodiments, an offset is applied to the time point to achieve the final J point.

Figure 5:
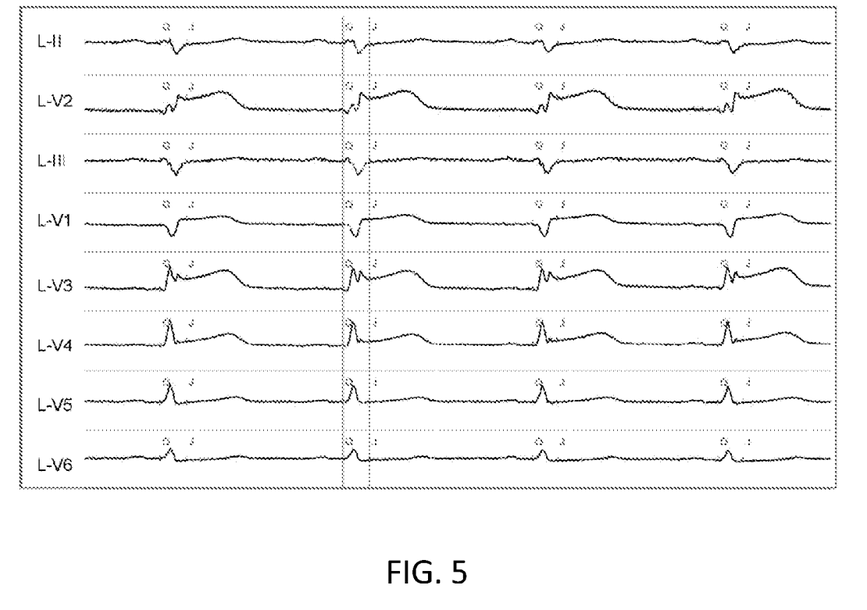
FIG. 5 is a graph of eight ECG signals labeled with the Q point and the J point detected by a Q, J detector.

With reference to FIG. 5, the results of Q, J detection on a beat-by-beat basis are shown. The traces from top down correspond to ECG signals for Lead II, $V_2$, III, $V_1$, $V_3$, $V_4$, $V_5$, and $V_6$, respectively. The Q and J points of each beat in the example are detected via a CWLS from all ECG leads. Further, the Q and J points are labeled on each lead of each beat.

Referring back to FIG. 2, an optional ST measurer 32 receives the Q and J points from the Q, J detector 24. For each lead, the ST measurer 32 determines the Iso-electric point from the Q point and measures the signal voltages at the Iso-electric point, J point, and J+x point. The Iso-electric point is obtained by applying an offset y to the Q point (i.e., Iso=Q−y). The offset y is typically 20 ms for adult subjects. The ST-segment level at the J point (ST_J) and the ST-segment level at the J+x point (ST_Jx) are then calculated for each lead.

Figure 6:
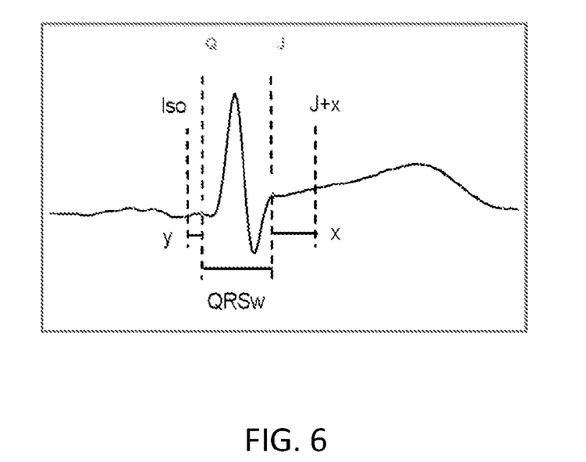
FIG. 6 is a graph of a beat-cycle waveform illustrating measured points for the Iso-electric point, the J point, and the J+x point.

In some embodiments, the ST-segment levels at J and J+x are calculated using Equations (4) and (5), respectively.

$$ST\_J_j = ecg_j[J] − ecg_j[Iso] \quad (4)$$

$$ST\_J_{x_j} = ecg_j[J+x] − ecg_j[Iso] \quad (5)$$

j is the lead number, $ST\_J_j$ is the ST segment level at J on lead j, x is a chosen time interval with a typical value of 60 or 80 ms, $ST\_Jx_j$ is the ST segment level at J+x on lead j, $ecg_j[J]$ and $ecg_j[J+x]$ are the lead j signal voltages at the J point and the J+x point, respectively, and $ecg_j[Iso]$ is the lead j signal voltage at the Iso point. With reference to FIG. 6, the measurement points for the Iso, J, and J+x points, which are used to calculate the ST-segment levels as J and J+x, are illustrated.

In other embodiments, the ST-segment levels at J and J+x are calculated using the median (or mean) value of the ECG signals in small windows surrounding the Iso, J, and J+x points. This is in contrast to using single point ECG signal values at Iso, J, and J+x points. A reasonable size for a small window is 40 ms and the window should be centered at the Iso, J, and J+x points.

Since the Iso-electric point is determined based on the Q-point, which is the dynamically-detected QRS onset of each considered beat, the Iso-electric point is reliable and stable even when the QRS morphology changes. The J point is determined directly for the QRS offset of each considered beat, so the J point can dynamically adapt to change in the QRS morphology.

An optional ST monitor 34 receives the ST_J and ST_Jx values, compares them to alarm criteria, and issues ST alarms when the alarm criteria is met. For example, an alarm can be issued when the ST_J and/or ST_Jx values fall outside predetermined ranges. The alarm criteria can be established according to clinical guidelines and/or ST elevation myocardial infarction (STEMI) criteria. The ST alarms are suitably generated to notify clinicians of an event.

An optional QRS width measurer 36 receives the Q and J points from the Q, J detector 24. For each lead, the QRS width (QRSw) is calculated from the Q and J points. In other words, the difference between the locations of the Q point and the J point is calculated. The QRS width can then employed for beat classification. It is a sensitive feature to distinguish beat types, such as a super-ventricular beat and a ventricular beat. Additionally, or alternatively, the QRS width can be employed by a QRS width monitor 38. The QRS width monitor 38 compares the QRS width to alarm criteria and issues a QRS alarm when the alarm criteria is met. Trending of the QRS width can be used to track gradual prolongation of myocardial depolarization, which may indicate worsening of myocardial condition.

The components of the EAS 14, including the receiver 16, the preprocessors 18, the beat selector 20, the Q, J detector 24, the ST measurer 32, ST monitor 34, the QRSw measurer 36 and the QRSw monitor 38, can be implemented in hardware, software, or a combination thereof. Where a component of the EAS 14 is implemented as software, a processor 40 of the EAS 14 executes computer executable instructions, stored on a memory 42, implementing the component. For example, the Q, J detector 24 can be implemented as computer executable instructions which are stored on the memory 42 and executed by the processor 40.

The system 10 can be deployed for patient monitoring in intensive care units (ICUs), operating rooms (ORs), general wards, a patient's home, and so on. Further, the system 10 can be used in clinical studies for investigating clinical outcomes of ischemia patients with ECG monitoring of ST-measurement at J+0. Further, in some embodiments the system 10 is integrated. For example, the sources 12 and the EAS 14 are combined.

Figure 7:
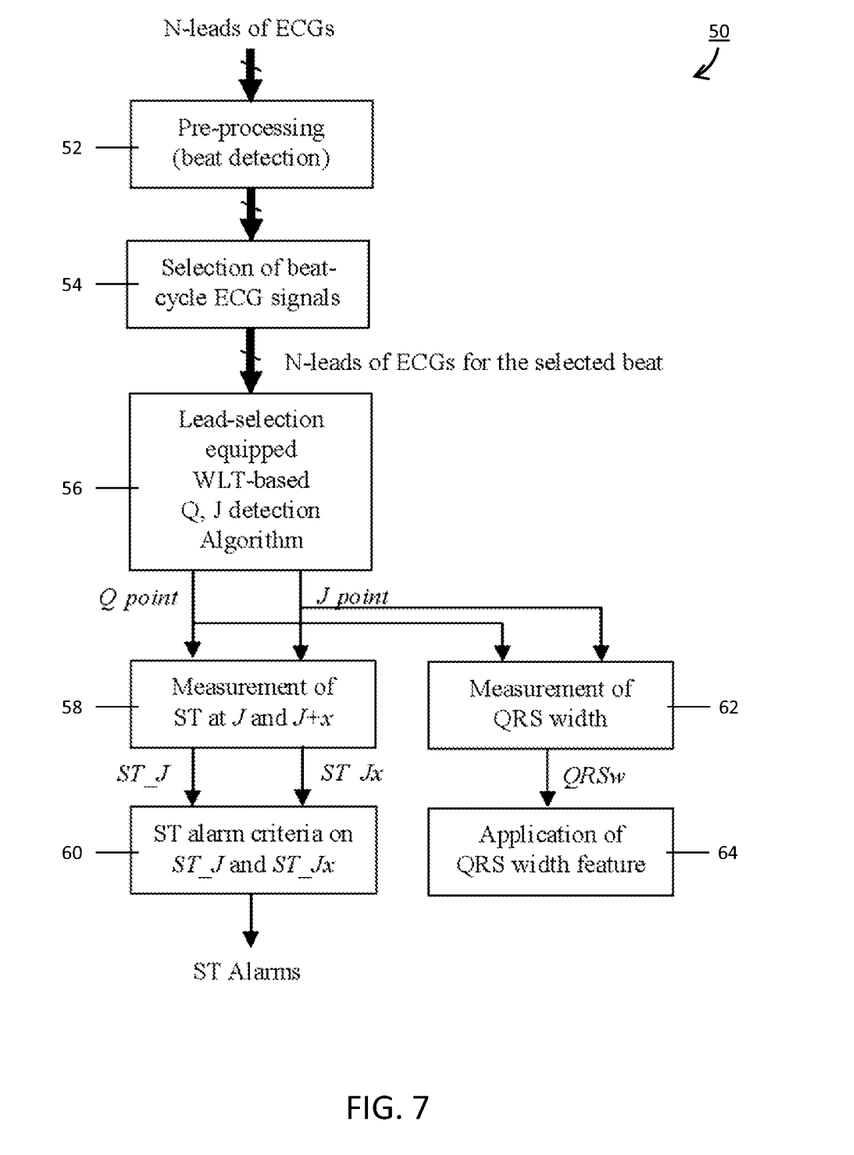
FIG. 7 is a block diagram of a method for measuring the ST-segment level and/or QRS width of an electrocardiogram.

With reference to FIG. 7, a method 50 for measuring the ST-segment level and/or QRS width of an electrocardiogram is provided. The method 50 is suitably performed by the EAS 14 and the constituent steps described hereafter correspond to components of the EAS 14 described heretofore. Further, the method 50 can be implemented as software, hardware or a combination thereof.

The method 50 includes preprocessing 52 N ECG waveforms of the electrocardiogram. The ECG waveforms correspond to different leads. The preprocessing 52 includes detecting and classifying each beat, as well as optionally filtering the waveforms to remove noise. A beat for consideration is selected 54 within the waveforms.

The beat under consideration can be manually specified, for example, using a user input device 22, or automatically specified according to one or more rules.

The Q point and the J point are detected 56 in the beat-cycle waveforms for the beat under consideration. In doing so, only beat-cycle waveforms corresponding to leads with good signal quality are employed for detection. Further, the beat-cycle waveforms with good signal quality are merged to a combined waveform length signal, which is used for detection.

The Q point and the J point are optionally employed to measure 58 the ST-segment level at the J point and/or the J+x point. ST alarms are then issued 60 conditionally depending upon whether the ST-segment levels match alarm criteria. Additionally, the Q point and the J point are optionally employed to measure 62 the QRS width, which is then applied 64 to beat classification and/or alarming. As to the latter, QRS width alarms are issued conditionally depending upon whether the QRS width matches alarm criteria.

As used herein, a memory includes one or more of a non-transient computer readable medium; a magnetic disk or other magnetic storage medium; an optical disk or other optical storage medium; a random access memory (RAM), read-only memory (ROM), or other electronic memory device or chip or set of operatively interconnected chips; an Internet/Intranet server from which the stored instructions may be retrieved via the Internet/Intranet or a local area network; or so forth. Further, as used herein, a processor includes one or more of a microprocessor, a microcontroller, a graphic processing unit (GPU), an application-specific integrated circuit (ASIC), a field-programmable gate array (FPGA), and the like; and a user input device includes one or more of a mouse, a keyboard, a touch screen display, one or more buttons, one or more switches, one or more toggles, and the like.

Test Results

The foregoing approach to measuring ST-segment level was tested using the ECG signals of averaged normal beats. The averaged normal beats were obtained by averaging the beat-cycle waveforms of individual normal beats in 15 second windows. The ECG signals were obtained from the European Society of Cardiology (ESC) ST-T Database. The ECS ST-T Database includes 90 ECG records, each including 2 hours of 2-channel ECG signals with cardiologist annotations for the ST-segment level at J+80 ms.

Figure 8:
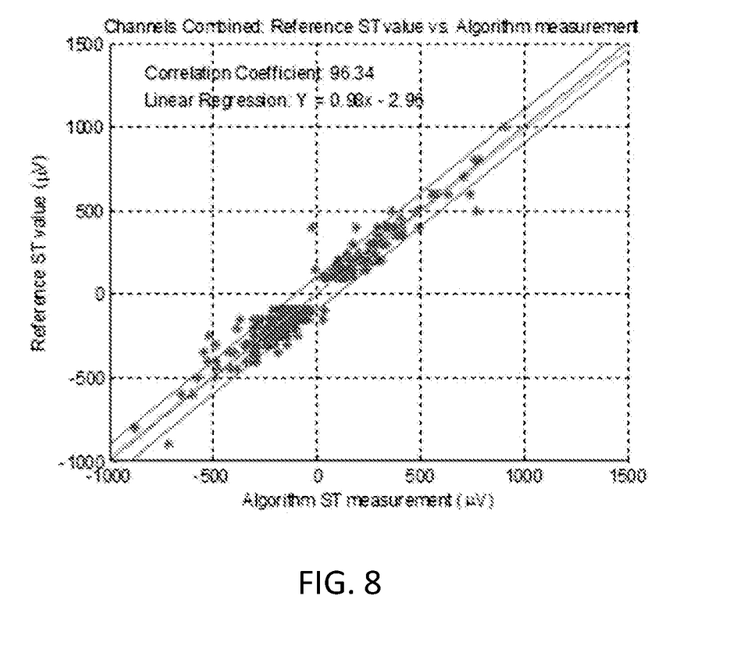
FIG. 8 is a scatter plot showing ST measurements at J+80 versus cardiologist annotations for the European Society of Cardiology ST-T Database.
Figure 9:
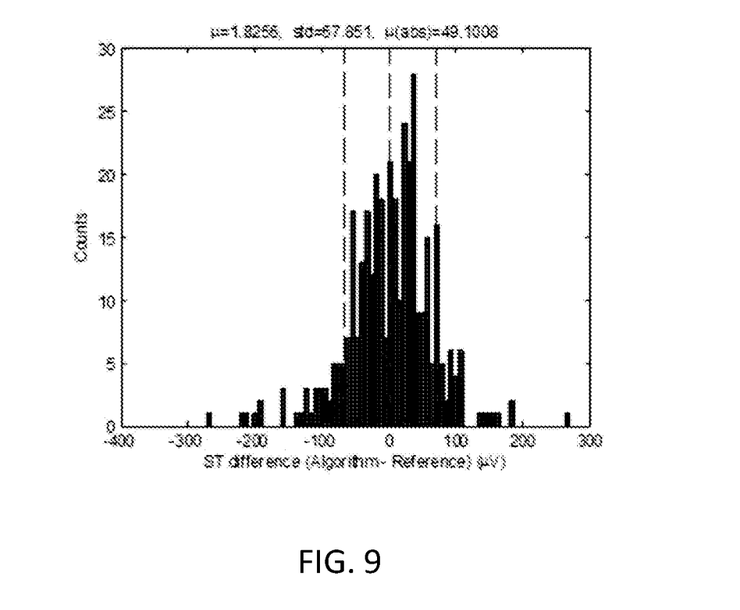
FIG. 9 is a histogram of the difference between ST measurement at J+80 and cardiologist annotations for the European Society of Cardiology ST-T Database.

With reference to FIG. 8, a scatter plot is illustrated showing ST measurements at J+80 ms achieved using the above described approach versus cardiologist annotations for both ECG channels of the 90 records in the ESC ST-T Database. The vertical axis is the ST value from the cardiologist and the horizontal axis is the ST measurement. From the scatter plot, the correlation coefficient is 96.3, the linear regress (LR) slope is 0.98, and the LR offset is −2.96 (μV). With reference to FIG. 9, a histogram of the difference between ST measurement at J+80 ms and cardiologist annotations is illustrated. The mean difference (μ), the standard deviation (std), and the mean absolute difference (μ(abs)) are 1.83, 67.9, and 49.1 (μV), respectively.

The foregoing approach to measuring ST-segment level was further tested using ECG signals obtained from a percutaneous transluminal coronary angioplasty (PTCA) database. The database includes 60 ECG records, each including 12-lead ECG signals recorded from adult subjects who were undergoing a PTCA procedure. The duration of the records ranged from 2:20 to 16:00 minutes. For each record, two 1-minute ECG regions were selected according to the signals' ST conditions. The first region was for the ST baseline and the second region was with ST elevation (or depression). In those two 1-minute regions of each record, a cardiologist annotated the Q and J points of each beat. According to the cardiologist annotated Q and J points, the ST values at J+0 and J+60 (ms) were generated for each beat and averaged in 15 second windows to generate reference ST annotations at J and J+60. The reference ST annotations at J+0 and J+60, for the 60 records of the PTCA database, were then compared with ST measurements at J+0 and J+60, respectively.

Figure 10:
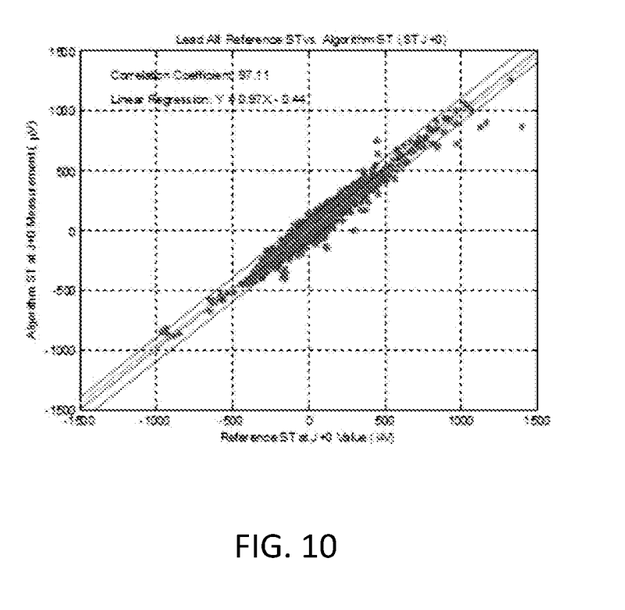
FIG. 10 is a scatter plot showing ST measurements at J+0 versus cardiologist annotations for a percutaneous transluminal coronary angioplasty database.
Figure 11:
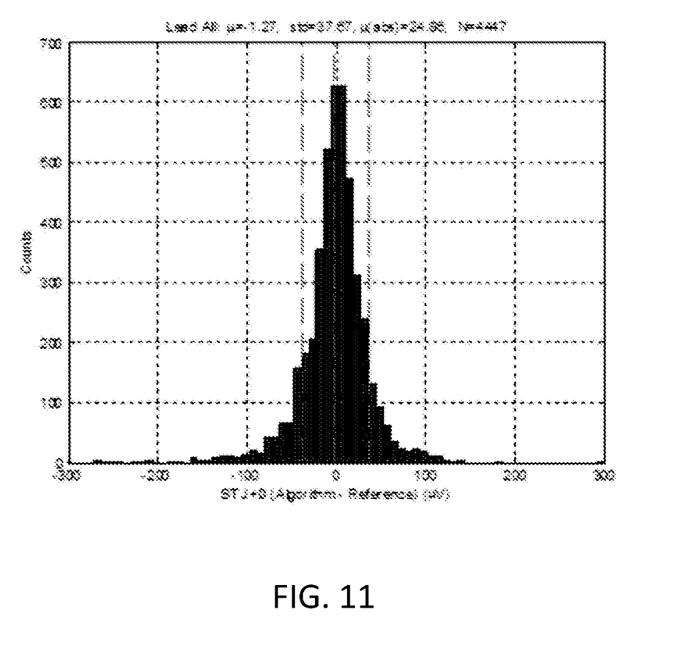
FIG. 11 is a histogram of the difference between ST measurement at J+0 and cardiologist annotations for a percutaneous transluminal coronary angioplasty database.

With reference to FIG. 10, a scatter plot is illustrated of the ST measurements at J+0 versus the reference ST annotations at J+0. The correlation coefficient, the LR slope and the LR offset are 97.11, 0.97 and −0.44 (µV), respectively. With reference to FIG. 11, a histogram of the difference between the ST measurements at J+0 and the reference ST annotations at J+0 is illustrated. The mean differences (µ), the standard deviation (std), and the mean absolute difference (µ(abs)) are −1.27, 37.67, and 24.86 (µV), respectively.

Figure 12:
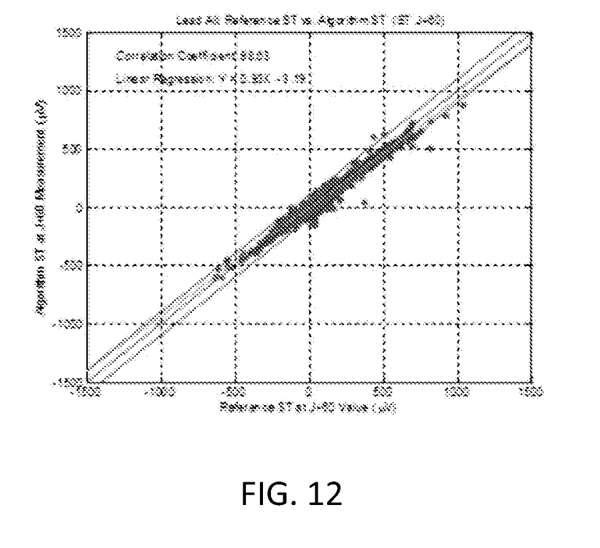
FIG. 12 is a scatter plot showing ST measurements at J+60 versus cardiologist annotations for a percutaneous transluminal coronary angioplasty database.
Figure 13:
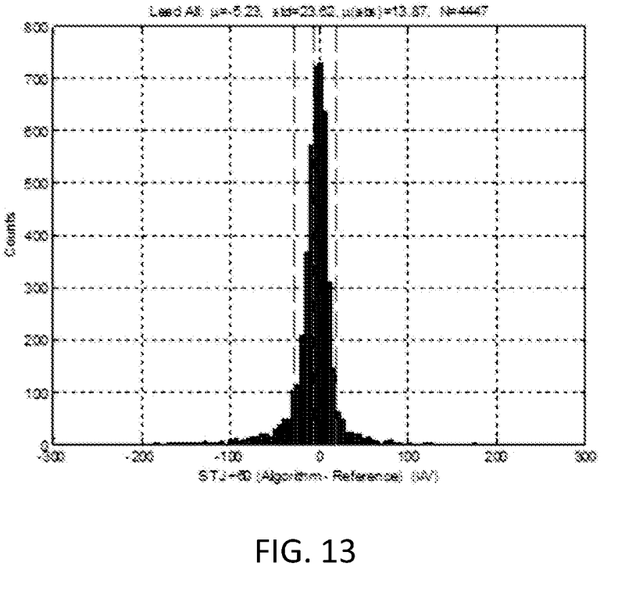
FIG. 13 is a histogram of the difference between ST measurement at J+60 and cardiologist annotations for a percutaneous transluminal coronary angioplasty database.

With reference to FIG. 12, a scatter plot is illustrated of the ST measurements at J+60 versus the reference ST annotations at J+60. The correlation coefficient, the LR slope and the LR offset are 98.63, 0.93 and −3.19 (µV), respectively. With reference to FIG. 13, a histogram of the difference between the ST measurements at J+60 and the reference ST annotations at J+60 is illustrated. The mean differences (µ), the standard deviation (std), and the mean absolute difference (µ(abs)) are −5.23, 23.62, and 13.87 (µV), respectively.

Figure 14:
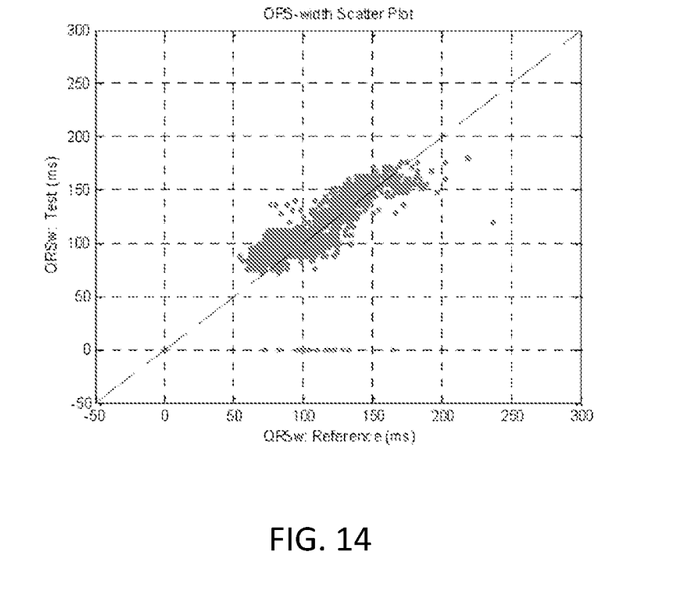
FIG. 14 is a scatter plot of measured QRS width versus reference QRS width for the MIT-BIH Arrhythmia Database.
Figure 15:
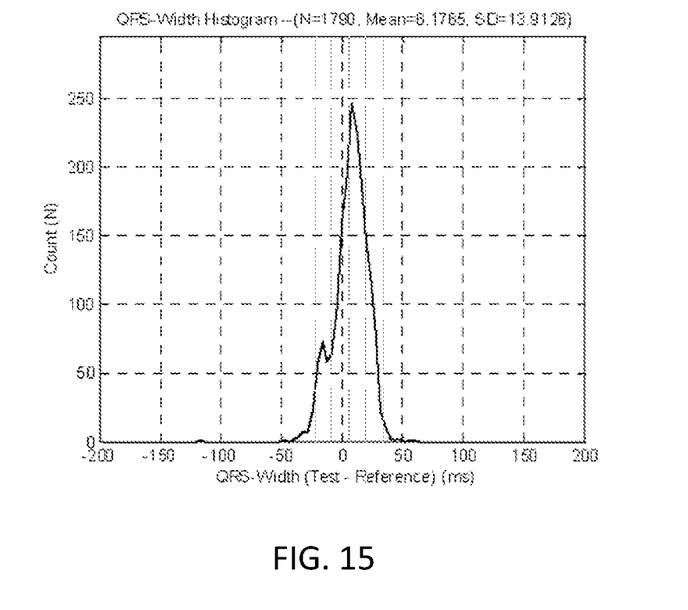
FIG. 15 is a histogram of the difference between measured QRS width and the reference QRS width for the MIT-BIH Arrhythmia Database.

The foregoing approach to measuring QRS width was tested using ECG signals from the MIT-BIH Arrhythmia Database. Twenty three records of 2-channel, 30-min ECG signals with various beat types, such as normal, premature ventricular contraction (PVC) and bundle branch block (BBB), were selected from the MIT-BIH Arrhythmia Database. For each of those twenty three records, cardiologists annotated the QRS onset and offset on 60-second ECG episodes (typically starting from 10:00) and the reference QRS widths were generated. The QRS width of those twenty three, 2-channel records was then measured in a beat-by-beat manner. Any beat type (i.e., not just normal beats) was considered. The resulting QRS width measurement from each beat was compared to the corresponding reference QRS width. A gross of 1790 beats were taken into account in the results. With reference to FIG. 14, a scatter plot of the measured QRS width versus the reference QRS width is provided. With reference to FIG. 15, a histogram of the difference between the measured QRS width and the reference QRS width is illustrated. The mean difference and standard deviation are 6.18 ms and 13.91 ms, respectively.

Figure 16:
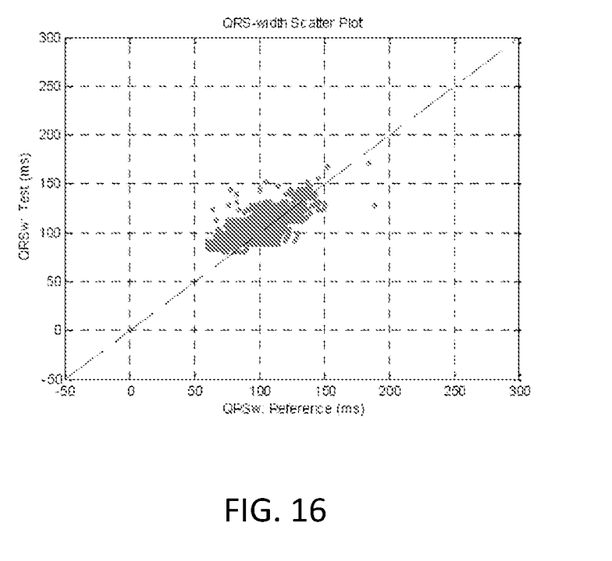
FIG. 16 is a scatter plot of measured QRS width versus the reference QRS width for a percutaneous transluminal coronary angioplasty database.
Figure 17:
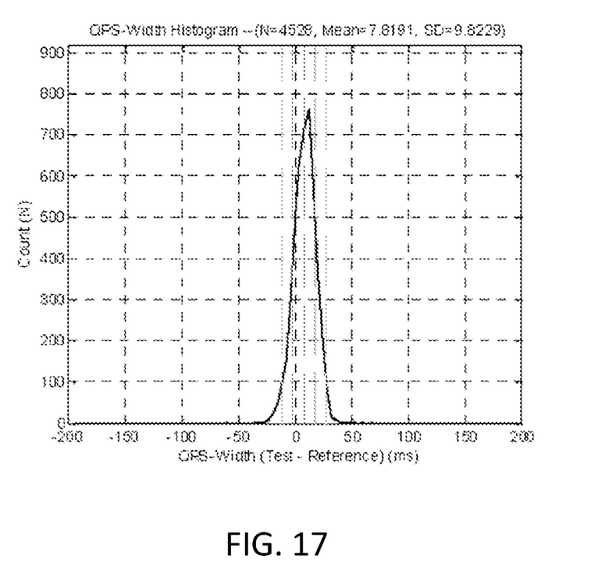
FIG. 17 is a histogram of the difference between measured QRS width and the reference QRS width for a percutaneous transluminal coronary angioplasty database.

The foregoing approach to measuring QRS width was further tested using ECG signals obtained from the PTCA database. Half of the records (i.e., 30 records) of the PTCA database were used. The QRS width of those thirty records was then measured using all channels in a beat-by-beat manner. The resulting QRS width measurement from each beat was compared to the corresponding reference QRS width. A gross of 4528 beats were taken into account in the results. With reference to FIG. 16, a scatter plot is illustrated of the measured QRS width versus the reference QRS width. With reference to FIG. 17, a histogram of the difference between the measured QRS width and the reference QRS width. The mean difference and standard deviation are 7.82 ms and 9.82 ms, respectively.

The test results of the ST measurements at J+80, J+60 and J+0 are excellent and satisfactory. It is particularly notable that satisfactory performance of the ST measurement at J (i.e., J+0) assures real-time monitoring of the ST-segment level at J and enabling use of the latest sensitive STEMI criteria. Further, the above QRS width test results show excellent and satisfactory performance of the QRS width detection.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

Having thus described the preferred embodiments, the invention is now claimed to be:

1. A system for determining Q and J points of an electrocardiogram (ECG), said system comprising:
at least one processor programmed to:
receive beat-cycle waveforms for a selected beat from a plurality of ECG leads;
determine a signal quality of each of the plurality of ECG leads based on at least one of high-frequency noise (HFN) level, low-frequency noise (LFN) level and QRS amplitude;
combine the beat-cycle waveforms of ECG leads with the determined signal quality meeting or exceeding a predetermined signal quality criteria; and,
identify the Q and J points on the combined beat-cycle waveform.

2. The system according to claim 1, wherein the signal quality of an ECG lead meets or exceeds the predetermined signal quality criteria if the HFN level of the ECG lead is less than a predetermined level, the LFN level of the ECG lead is less than a second predetermined level, and the QRS amplitude of the ECG lead is larger than a third predetermined level.

3. The system according to claim 1, wherein the combining uses a waveform length transform (WLT) to generate the combined beat-cycle waveform as a single-channel combined waveform length signal CWLS[i] according to: t,?
where i is a time index, w is a window in units of samples, j=1, ..., M indexes the M ECG leads with the signal quality meeting or exceeding the predetermined signal quality criteria, $\Delta y_{j,k} = ecg_j[k] - ecg_j[k-1]$ is the ECG lead j waveform at sample k, and $\Delta t$ is the sampling interval.

4. The system according to claim 1, wherein the identifying of the Q and J points includes at least one of:
identifying QRS offset of the combined beat-cycle waveform, the QRS offset corresponding to the J point; and,
identifying QRS onset of the combined beat-cycle waveform, the QRS onset corresponding to the Q point.

5. The system according to claim 1, wherein the identifying of the Q and J points includes:
searching backward in time along the combined beat-cycle waveform from a point on the combined beat-cycle waveform with a maximum value of the combined beat-cycle waveform for a second point with a value equal to or less than about 99% of the maximum value, the second point corresponding to the J point.

6. The system according to claim 1, wherein the identifying of the Q and J points includes:
determining a point on a QRS complex of the combined beat-cycle waveform with a value of half a maximum value of the combined beat-cycle waveform;
generating a virtual line extending from the determined point to a second point on the combined beat-cycle waveform, the second point before the QRS complex; and,
determining a time point with a maximum distance between the virtual line and the combined beat-cycle waveform, the time point corresponding to the Q point.

7. The system according to claim 1, wherein the processor is further programmed to at least one of:
determine ST-segment level of the beat from the Q and J points; and
determine QRS width of the beat from the Q and J points.

8. The system according to claim 7, wherein the processor is further programmed to:
issue an alarm in response the ST-segment level and/or the QRS width matching alarm criteria.

9. The system according to claim 1, wherein the beat-cycle waveforms are received from an electrocardiograph.

10. A method for determining Q and J points of an electrocardiogram (ECG), said method comprising:
receiving beat-cycle waveforms for a selected beat from a plurality of ECG leads;
determining a signal quality of each of the plurality of ECG leads;
combining the beat-cycle waveforms of ECG leads with the determined signal quality meeting or exceeding a predetermined signal quality criteria while excluding ECG leads with the determined signal quality not meeting the predetermined signal quality criteria; and,
identifying the Q and J points on the combined beat-cycle waveform.

11. The method according to claim 10, wherein the determining includes:
determining, for each ECG lead, at least one of high-frequency noise (HFN) level, low-frequency noise (LFN) level and QRS amplitude.

12. The method according to claim 11, wherein the signal quality of a lead meets or exceeds the predetermined signal quality criteria if the HFN level of the lead is less than a predetermined level, the LFN level of the lead is less than a second predetermined level, and the QRS amplitude of the lead is larger than a third predetermined level.

13. The method according to claim 10, wherein the combining uses a waveform length transform.

14. The method according to claim 10, wherein the identifying of the Q and J points includes:
searching backward in time along the combined beat-cycle waveform from a point on the combined beat-cycle waveform with a maximum value of the combined beat-cycle waveform for a second point with a value equal to or less than about 99% of the maximum value, the second point corresponding to the J point.

15. The method according to claim 10, wherein the identifying of the Q and J points includes:
determining a point on a QRS complex of the combined beat-cycle waveform with a value of half a maximum value of the combined beat-cycle waveform;
generating a virtual line extending from the determined point to a second point on the combined beat-cycle waveform, the second point before the QRS complex; and,
determining a time point with a maximum distance between the virtual line and the combined beat-cycle waveform, the time point corresponding to the Q point.

16. The method (50) according to claim 10, further including at least one of:
determining ST-segment level of the beat from the Q and J points; and
determining QRS width of the beat from the Q and J points.

17. The method according to claim 16, further including:
issuing an alarm in response the ST-segment level and/or the QRS width matching alarm criteria.

18. One or more processors programmed to perform the method according to claim 10.

19. A non-transitory computer readable medium carrying software which controls one or more processors to perform a method for determining Q and J points of an electrocardiogram (ECG), said method comprising:
receiving beat-cycle waveforms for a selected beat from a plurality of ECG leads;
determining a signal quality of each of the plurality of ECG leads wherein the determining includes:
determining, for each ECG lead, high-frequency noise (HFN) level, low-frequency noise (LFN) level and QRS amplitude, wherein the signal quality of an ECG lead meets or exceeds the predetermined signal quality criteria if the HFN level of the ECG lead is less than a predetermined level, the LFN level of the ECG lead is less than a second predetermined level, and the QRS amplitude of the ECG lead is larger than a third predetermined level;
combining the beat-cycle waveforms of ECG leads with the determined signal quality meeting or exceeding a predetermined signal quality criteria while excluding ECG leads with the determined signal quality not meeting the predetermined signal quality criteria to generate a single-channel combined beat-cycle waveform signal as a function of time; and,
identifying the Q and J points on the single-channel combined beat-cycle waveform signal as a function of time.

* * * * *